US006485976B1

(12) United States Patent
Nadler et al.

(10) Patent No.: US 6,485,976 B1
(45) Date of Patent: Nov. 26, 2002

(54) USE OF ADENO-ASSOCIATED VIRUS (AAV) TO DELIVER GENES

(75) Inventors: Jerry L. Nadler, Charlottesville, VA (US); David Bleich, Pasadena, CA (US); Konkal-Matt R. Prasad, Charlottesville, VA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/559,915

(22) Filed: Apr. 28, 2000

Related U.S. Application Data

(60) Provisional application No. 60/132,123, filed on Apr. 30, 1999.

(51) Int. Cl.[7] .......................... C12N 15/63; C12N 5/00; C12P 19/34; C12Q 1/68; C07H 21/02

(52) U.S. Cl. .......................... 435/455; 435/6; 435/91.1; 435/366; 435/378; 536/23.1

(58) Field of Search .......................... 435/6, 69.1, 70.1, 435/91.1, 455, 456, 366, 375, 320.1; 536/23.1

(56) References Cited

U.S. PATENT DOCUMENTS 6,001,647 A * 12/1999 Peck et al. .................. 435/325
6,110,743 A * 8/2000 Levine et al. ............... 435/456

FOREIGN PATENT DOCUMENTS

WO          98/48009          10/1998

OTHER PUBLICATIONS

John E. Murphy et al., Long–term correction of obesity and diabetes in genetically obese mice by a single intramuscular injection of recombinant adeno–associated virus encoding mouse leptin, Proc. Natl Acad. Sci USA, vol. 94, pp. 13921–13926.*
R.J. Bartlett et al., Successful Transduction of Human Islets With Recombinant Adeno Associated Virus, XP–002151578.*
Palu et al. J. Biotech., vol. 68, pp. 1–13, 1999.*
Verma et al. Nature, vol. 389, pp. 239–242, 1997.*
Branch, A. Trends in Bioch. Sci., vol. 23, pp. 45–50, 1998.*
Friedmann, T. Scientific American, June vol., pp. 96–101, 1997.*
Schofield et al. Science, vol. 270, pp. 404–410, 1995.*
Crystal, R.G. Science, vol. 270, pp. 404–410, 1995.*
Crooke, S.T. Antisense Research and Application, Chapter 1, pp. 1–50, Published by Springer–Verlag, 1998.*
Murphy et al., "Long–term correction of obesity and diabetes in genetically obese mice by a single intramuscular injection of recombinant adeno–associated virus encoding mouse leptin," Proc. Natl. Acad. Sci. USA 94:13921–13926, Dec. 1997.

Gallichan et al., "Lentivirus–Mediated Transduction of Islet Grafts with Interleukin 4 Results in Sustained Gene Expression and Protection from Insulitis," Human Gene Therapy 9:2717–2726, Dec. 10, 1998.
Bartlett et al., "Successful Transduction of Human Islets with Recombinant Adeno Associated Virus," Cell Transplantation 8(2):183, Mar. 1999 (XP002151578), Fourth International Congress of the Cell Transplant Society, Montreux, France, Mar. 21–24, 1999.
Block et al., High Efficiency Genomic Transduction of Intact Pancreatic Islets in Long Term Culture with Recombinant Adeno–Associated Virus Vectors (rAAV), Transplantation, 67:7 s207, Apr. 15, 1999, Abstract. (XP–002151579).
Hohmeier et al., "Stable Expression of Manganese Superoxide Dismutase (MnSOD) in Insulinoma Cells Prevents IL–1β–Induced Cytotoxicity and Reduces Nitric Oxide Production," J. Clin. Invest. 101(9):1811–1820, May 1, 1998.
Hotta et al., "Pancreatic β Cell–specific Expression of Thioredoxin, and Antioxidative and Antiapoptotic Protein, Prevents Autoimmune and Streptozotocin–induced Diabetes," J. Exp. Med. 188(8):1445–1451, Oct. 19, 1998.
Yasuda et al., "Local Expression of Immunoregulatory IL–12p40 Gene Prolonged Syngeneic Islet Graft Survival in Diabetic NOD Mice," J. Clin. Invest. 102(10):1807–1814, Nov. 1998.
Lenzen et al., "Low Antioxidant Enzyme Gene Expression in Pancreatic Islets Compared with Various Other Mouse Tissues," Free Radical Biology & Medicine, 20(3):463–466, 1996.
Benhamou et al., "Adenovirus–mediated catalase gene transfer reduces oxidant stress in human, porcine and rat pancreatic islets," Diabetologia 41(9):1093–1100, 1998.
Moritani et al., "Prevention of Adoptively Transferred Diabetes in Nonobese Diabetic Mice with IL–10–Transduced Islet–specific Th1 Lymphocytes," J. Clin. Invest. 98(8):1851–1859, Oct. 1996.
Shimabukuro et al., "Leptin– or Troglitazone–induced Lipopenia Protects Islets from Interleukin 1β Cytotoxicity," J. Clin. Invest. 100(7):1750–1754, Oct. 1997.

(List continued on next page.)

*Primary Examiner*—Sean McGarry
*Assistant Examiner*—Jane Zara
(74) *Attorney, Agent, or Firm*—Rothwell, Figg, Ernst & Manbeck, P.C.

(57) ABSTRACT

This invention pertains to a method of protecting pancreatic β-cells from immune system-mediated cell damage through transduction of the cells with an adeno-associated viral vector encoding cytoprotective genes. These protected cells are suitable for transplantation into mammals and will be protected from rejection by the host. The method also may be used to protect pancreatic islet β-cells in situ for the primary prevention of immune-mediated destruction which leads to Type 1 diabetes. Pancreatic β-cells may be transduced with AAV vectors according to the invention for in vivo or ex vivo gene therapy.

18 Claims, 9 Drawing Sheets

OTHER PUBLICATIONS

Bergmann et al., "Cytotoxic action of II–1β against pancreatic islets is mediated via nitric oxide formation and is inhibited by $N^G$–monomethyl–L–arginine," FEBS 299(1):103–106, 1992.

Burkart et al., "Mice lacking the poly(ADP–ribose) polymerase gene are resistant to pancreatic beta–cell destruction and diabetes development induced by streptozocin," Nature Medicine 5(3):314–319, Mar. 1999.

McDaniel et al., "Cytokines and nitric oxide in islet inflammation and diabetes," Proceedings of the Society for Experimental Biology and Medicine 211(1):24–32, 1996, Abstract.

Bleich et al., The role of 12–lipoxygenase in pancreatic β–cells (Review) International Journal of Molecular Medicine 1:265–272, 1998.

Ju et al., "Transduction of non–dividing adult human pancreatic beta cells by an integrating lentiviral vector," Diabetologia 41(6):736–9 Jun. 1998, Abstract.

Prasad et al., "Novel Method of Gene Delivery to Pancreatic Beta Cells," Diabetes 48(supp. 1):A58, 1999, Abstract. (XP–002152056).

Bleich et al., "Resistance to type 1 diabetes induction in 12–lipoxygenase knockout mice," J. Clin. Invest. 103(10):1431–1436, May 1999.

International Search Report for PCT/US 00/11356, dated Nov. 24, 2000.

Bankiewicz, Kryzysztof S., et al., (1997), "Practical Aspects of the Development of ex Vivo and in Vivo Gene Therapy for Parkinson's Disease," Experimental Neurology, Article No. EN966401, 147–156, vol. 144.

Chatterjee, Saswati et al., (1992) "Dual Target Inhibition of HIV–1 in Vitro by Means of an Adeno–Associated Virus Antisense Vector," Science, vol. 258:1485–1488.

During, Matthew J., et al., (1996), "Adeno–Associated Virus Vectors for Gene Therapy of Neurodegenerative Disorders," Clinical Neuroscience, vol. 3, 292–300.

Gu, JL, et al., (1995), "Ribozyme–mediated Inhibition of Expression of Leukocyte–type 12–lipoxygenase in Porcine Aortic Vascular Smooth Muscle Cells," Circulation Research, vol. 77, No. 1, 14–20.

Hallek, Michael, et al., (1996), "Recombinant adeno–associated virus (rAAV) vectors for somatic gene therapy: recent advances and potential clinical applications," Cytokines and Molecular Therapy, vol. 2, 69–79.

Hayashi, S., et al., (1997), "Adenovirus–Mediated Gene Transfer of Antisense Ribozyme for α(1,3) Galactosyltransferase Gene and α(1,2)Fucosyltransferase Gene in Zenotransplantation," Elsevier, 2213. (Transplantation Proc. 29.2213).

LaFace, Drake et al., (1988) "Gene Transfer into Hematopoietic Progenitor Cells Mediated by an Adeno–Associated Virus Vector," Virology, vol. 162, 483–486.

Lubovy, M. et al., (1996) "Stable transduction of recombinant adeno–associate virus into hematopoietic stem cells from normal and sickle cell patients," Biology of Blood and Marrow Transplantation vol. 2, 24–30.

McGown, Thomas J. et al., (1996) "Differential and persistent expression patterns of CNS gene transfer by an adeno–associated virus (AAV) vector," Brain Research, vol. 713, 99–107.

Nakayama, M., et al., (1998), "Cyclooxygenase–2 inhibition prevents delayed death of CA1 hippocampal neurons following global ischemia," Proc. Nat. Acad. Sci. USA, vol. 95, 10954–10959.

Naldini, L., et al. (1996), "In Vivo Gene Delivery and Stable Transduction of Nondividing Cells by a Lentiviral Vector," Science, vol. 272, 263–267.

Prince, H. Miles, (1998), "Gene Transfer: A Review of Methods and Applications," Pathology, vol. 3, 335–347.

Robbins, Paul D., et al. (1998), "Viral Vectors for Gene Therapy," Pharmacol. Ther., vol. 80, No. 1, 35–47.

Shimabukuro, M., et al. (1997), "Leptin– or Troglitazone–induced Lipopenia Protects Islets from Interleukin 1β Cytotoxicity," Journal of Clinical Investigation, vol. 100, No. 7, 1750–1754.

Smith, D.K., et al. (1997), "Interleukin–4 or Interleukin–10 Expressed From Adenovirus–Transduced Syngeneic Islet Grafts Fails to Prevent β Cell Destruction in Diabetic Nod Mice," Transplantation, vol. 64, No. 7 1040–1049.

Tahara, H., et al. (1992), "Islet Cell Transplantation Facilitated by Gene Transfer," Transplantation Proceedings, vol. 24, No. 6, 2975–2976.

von Herrath, Matthias G., et al. (1997), "Expression of Adenoviral E3 Transgenes in β Cells Prevents Autoimmune Diabetes," Proc. Natl. Acad. Sci. USA, vol. 94, 9808–9813.

Wong, C.A. et al., (1998) "Transfer into Quiescent CD34+ CD38– Hematopoietic Progenitor Cells with Adeno–Associated Virus Vectors," Blood, vol. 92(10), Suppl. 1, Abstract #2738.

Xi, Xu Guang, et al. (1993), "Retroviral–Mediated Gene Transfer of the Porcine Choline Acetyltransferase: A Model to Study the Synthesis and Secretion of Acetylcholine in Mammalian Cells," Neurol.n Chem. Int., vol. 22, No. 5, 511–516.

Zhou, Shang Zhen et al., (1994) "Adeno–associated Virus 2–mediated High Efficiency Gene Transfer into Immature and Mature Subsets of Hematopoietic Progenitor Cells in Human Umbilical Cord Blood," J. Exp. Med., vol. 179, pp 1867–1875.

* cited by examiner

293 CELLS TRANSDUCED
WITH vAAV βgal

293 CELLS TRANSDUCED
WITH vAAV βgal

RIN-m5F CELLS TRANSDUCED
WITH vAAV βgal

RIN-m5F CELLS TRANSDUCED
WITH vAAV βgal

INS-1 CELLS TRANSDUCED
WITH vAAV βgal

INS-1 CELLS TRANSDUCED
WITH vAAV βgal

DISPERSED RAT ISLET CELLS
TRANSDUCED WITH vAAV βgal

DISPERSED RAT ISLET CELLS
TRANSDUCED WITH vAAV βgal

USE OF ADENO-ASSOCIATED VIRUS (AAV) TO DELIVER GENES

CROSS-REFERENCE TO RELATED APPLICATIONS

This application is related to pending prior provisional application Ser. No. 60/132,123, filed Apr. 30, 1999.

BACKGROUND OF THE INVENTION

1. Technical Field

This application relates to the field of genetic modification. In particular, the invention disclosed herein provides a method of transducing cells with cytoprotective genes using adeno-associated viral vectors. Specifically, in a preferred embodiment the invention relates to a method of preventing or reducing the rejection of grafted insulin-producing pancreatic β-cells and islets by transduction of the grafted cells with cytoprotective genes. In another preferred embodiment, the invention relates to a method of protecting pancreatic islet β-cells from immune destruction in a patient to protect against the development of Type 1 diabetes.

2. Description of the Background Art

Type 1 diabetes is an autoimmune disease that ultimately results in destruction of the insulin producing β-cells in the pancreas. In type 1 diabetes, invading cells, primarily lymphocytes and macrophages, enter the islets and release toxic substances called cytokines which in turn set off an inflammatory reaction. Cytokines and immune signals play an important role in the overall defense mechanisms of the body, but can also be released in an unregulated fashion, leading to pancreatic islet cell damage in Type 1 diabetes or destruction of transplanted islet cells. Cytokines or other immune factors may damage the islets directly by stimulating "death" signals within the insulin producing β-cells or indirectly by causing other non-β-cells to produce a milieu that is cytotoxic to β-cells. In either case, destruction of the insulin-producing β-cells follows, along with the well known sequelae of hyperglycemia.

Although patients with Type 1 diabetes may be treated adequately with insulin injections or insulin pumps, these therapies are only partially effective. Insulin replacement via insulin or pump cannot fully reverse the defect in vascular endothelium found in the hyperglycemic state. Pieper et al., *Diabetes Res. Clin. Pract.* Suppl.:S157–S162 (1996). In addition, frequent hyper- and hypoglycemia typically occurs despite intensive home blood glucose monitoring. Finally, careful dietary constraint is needed to maintain an adequate ratio of calories consumed to insulin. This often causes major psychosocial stress for many diabetic patients. Development of methods to transplant functional pancreatic islets into diabetic patients would overcome most of these problems and result in improved life expectancy and quality of life.

The approach taken with this invention offers numerous advantages lacking in prior art therapies currently available and improves the success of known treatments such as islet cell transplantation. Currently, most treatments and therapy of diabetes focus on direct insulin replacement. Unfortunately, transplanted allo- or xenogeneic pancreatic islet cells, like whole-organ transplants, are subject to graft rejection as are other solid organ transplants.

The only viable method currently available in the prior art of preventing transplant rejection involves systemic immunosuppressive therapy, however immunosuppression can have serious, long-term effects on the graft recipient. Research aimed at the protection of transplanted allogeneic human pancreatic islets through genetic manipulation of the transplanted cells likewise has focussed on general immunosuppression. For example, Tahara et al. (*Transplantation Proc.* 24(6):2975–2976 (1992)) have expressed the immunosuppressive cytokine IL-10 in cultured cells using both retroviral and adeno-associated viral vectors to resolve the problems caused by the immune response to the transplanted cells. However, this report did not provide any evidence whether adeno-associated vectors could successfully deliver genes to β-cells or to pancreatic islets.

Immune-induced islet cytotoxicity plays a significant role in both autoimmune β-cell destruction in Type 1 diabetes and acute graft rejection after β-islet transplantation. General immunosuppression methods are designed to combat this toxicity. It is known that pancreatic β-cells, whether native or transplanted, undergo inflammatory damage and cell death upon chronic exposure to cytotoxic cytokines such as interleukin-1β (IL-1β) (Dunger et al., *J. Autoimmunity* 9:309–313 (1996); Mandrup-Poulsen et al., *Diabetologia* 29:63–6 (1986)). Cytokine treated islets in vitro demonstrate morphologic evidence of apoptosis such as nuclear condensation, intracytoplasmic vacuole formation, mitochondrial swelling, insulin degranulation, and preservation of the cell membrane when viewed under the electron microscope. (Ling et al., *Diabetes* 42:56–65 (1993); Fehsel et al., *Diabetes* 42:496–500 (1993)). A proposed method of circumventing the rejection mechanism without systemic immunosuppression involves introducing cytoprotective genes such as immunosuppressive cytokines into the donor tissue by means of a viral vector. Methods discussed in the prior art have used retroviral (including lentiviral) and adenoviral vectors. See e.a. Tahara et al., *Transplantation Proc.* 24(6):2975–2976 (1992); Smith et al., *Transplantation* 64:1040–1049 (1997); Hayashi, *Transplantation Proc.* 29:2213 (1997); Naldini, *Science* 272:263–267 (1996); Xi, *Neurochem. Int.* 22(5):511–516 (1993). Hayashi et al. have suggested adenovirus-mediated transduction of an antisense ribozyme for both the α(1,3)-galactosyl transferase gene and the α(1,2)-fucosyl transferase gene to xenogeneic cells and organs to inhibit hyperacute rejection.

For successful protection of pancreatic islets by genetic transduction, the vector used must be non-pathogenic, must be capable of stable gene expression, should not be inflammatory or cause the expression of immunogenic peptides and of course must be able to infect pancreatic β-cells. All the vector types currently proposed for transfer of genes to pancreatic β-cells lack at least one of the above properties which are desired for use in protection of pancreatic islets by genetic transduction.

Relatively few studies have used viral vectors to introduce transgenes into pancreatic islets. Csete and colleagues (*Transplantation* 59(2): 263–268 (1995)) showed that adenoviral vectors could effectively transfer *E. coli* β-galactosidase (β-gal) into mouse islets for up to 10 days in culture and that islet insulin secretion was not impaired by the viral DNA. Gene expression was confirmed by the demonstration of β-gal mRNA and high levels of functional β-gal protein. After 10 days, the β-gal protein returned to pre-transfection levels, indicating that the transgene was not incorporated into the host genome. Adenovirus-mediated gene transfer also has been achieved in mouse islets using a β-gal reporter gene by Sigalla and colleagues (*Human Gene Therapy* 8(13):1625–1634 (1997)). Transduced islets had normal in vitro glucose-stimulated insulin secretion and were able to normalize blood glucose when transplanted into syngeneic and allogeneic streptozotocin-induced diabetic mice.

In addition, ex vivo gene transfer into mouse islets has been successfully performed using an adenoviral vector with approximately 50% of the islets showing positive staining for β-gal which was detectable for 8 weeks (Smith et al., Transplantation 64(7):1040–1049 (1997)). Gene transfer to human pancreatic α- and β-cells have also been demonstrated using adenovirus-polylysine/DNA complexes with peak levels of expression lasting for 5–7 days (Becker et al., J. Biol. Chem. 269(33):21234–21238 (1994)). There, both polycationic liposome- and adenoviral-mediated gene transfer yielded 50–70% βgal positive cells, but chloramphenicol acetyl transferase activity degenerated after 5–7 days indicating that the transgene was not incorporated into the host genome. In addition, intact human islets showed lower transduction efficiencies than dispersed islet cells, possibly due to fewer cells being exposed to virus. In any case, adenoviral vectors were not capable of long-term, stable integration of genes into the islet cells.

Aside from providing only transient expression, adenoviruses have been shown to cause inflammation which subsequently can cause the same immune-mediated graft rejection which treatment would be designed to prevent. Retroviruses are pathogenic, particularly the lentiviruses. Moreover, for proper integration into the host genome, retroviruses require their natural enhancer/promoter complexes. This may interfere with expression of the inserted gene and also restricts the potential size of any inserted gene.

On the other hand, adeno-associated virus (AAV) has several features that make it an attractive vector for transferring therapeutic or protective genes. AAV is a replication-defective DNA virus with a 4.7 kb genome. This small genome allows for early manipulation by standard recombinant methodology. It is a human parvovirus consisting of three structural genes, rep, lip, and cap, and containing palindromic inverted terminal repeats (ITR). AAV vector is nonpathogenic because it requires co-infection with a helper virus for productive infection, typically adeno virus or herpes simplex virus, but AAV does not require helper virus to become integrated into a host cell genome or to persist in host cells. Without a helper virus, AAV integrates into the host genome and remains as a provirus. AAV transduction therefore can lead to long term, stable gene expression, even in non-dividing cells, a necessary feature since pancreatic β-cells are non-dividing. Replication, packaging and integration of AAV does not require the AAV enhancer/promoter elements for integration into the host genome. Only the natural terminal repeats are required, therefore genes can be inserted along with their own natural regulatory elements, greatly increasing the likelihood of stable wild-type expression. Furthermore, AAV vectors frequently integrate as multi-copy tandem repeats, unlike retroviral vectors, enhancing transgene expression. Importantly, unlike adenoviral vectors, AAV does not lead to inflammation in target cells.

Other advantages to AAV transduction include the fact that DNA polymerase, the enzyme responsible for AAV replication, has a 10,000 fold lower error rate than reverse transcriptase. There is evidence that infection with wild-type AAV inhibits transformation by papilloma viruses and activated H-ras oncogene in vitro, while epidemiological studies suggest that prior infection in humans may confer oncoprotection. AAV vectors have recently been approved for use in clinical gene therapy for cystic fibrosis based on recent observations of long-term in vivo expression of an AAV vector-encoded cystic fibrosis transmembrance conductance regulatory gene in rabbit airway epithelial cells. Flotte et al., Proc. Natl. Acac. Sci. USA 90:10613–10617 (1993).

Wild type AAV is unique among eukaryotic viruses in its ability to integrate site-specifically into the AAVS 1 site of the human chromosome 19. Although AAV vectors do not appear to integrate into the same chromosomal site as wild-type AAV, little is known about the precise mechanism of vector integration. Integration is mediated by the virus-encoded rep78 protein, which recognizes consensus sequences on both the AAV ITR and AAVS1. Rep78 possesses site specific, DNA-binding, endonuclease and helicase activities and is postulated to form a bridge between the wild type AAV genome and AAVS1 to facilitate site-specific integration.

Inhibition of HIV replication and expression has been attempted using an AAV vector. The vector delivered an antisense gene targeting the RNA sequences present in the 5'- and 3'- regions of HIV-1 mRNA (Fisher-Adams et al., Blood 88:492, 1996). Transduced cells showed specific and significant inhibition of HIV LTR-directed gene expression and virus replication. AAV transduction was not associated with any toxicity or alterations of cell viability, growth inhibition or heterologous transcription. This study represented the first use of an AAV-based anti-HIV vector. AAV vectors have been used to express human tyrosine hydroxylase II gene, factor IX, neuropeptide Y, human glucocerebrosidase and arylsulfatase A, the CFTR gene, β-globin and antisense to α-globin. However, it is not known whether AAV can successfully transduce pancreatic islets or isolated beta cells.

Recent reports have demonstrated the use of AAV vectors for sustained gene expression in porcine myocardium and skeletal muscle McLaughlin et al., Virology 162:483–486 (1988); Kaplitt et al., Ann. Thorac. Surg. 62:1669–1676 1996)). Infusion of an AAV vector into porcine cardiac muscle cells as well as coronary arteries has resulted in sustained gene expression for at least 6 months (Kessler et al., Proc. Natl. Acad. Sci. USA 93:14082–14087 (1996)). March and colleagues also demonstrated the feasibility of using AAV as a gene transfer vector for vascular smooth muscle cells (March et al., Clin. Res. 40:358A (1992)). AAV also has been used to deliver genes into kidney cells, neuronal cells, airway epithelial cells, and liver hepatocytes. Larger et al., Exp. Nephol. 6(3):189–194 (1998); Chamberlin et al., Brain Res. 793(1–2):169–175 (1998); Teramoto et al., J. Virol. 72:8904–8912 (1998); Sugiyama et al., Horm. Metab. Res. 29:599–603 (1997)). However, no reports of attempts to transduce pancreatic β-cells have been made, nor has it been shown that AAV vectors are capable of transferring genes to β-cells or pancreatic islets.

SUMMARY OF THE INVENTION

Accordingly, the present invention provides a method for protecting pancreatic islet β-cells from immune system-mediated toxicity by transducing the cells with an adeno associated virus vector having inserted therein genetic material encoding a product which reduces immune system-mediated cell toxicity in the transduced cells. Exemplary genetic material includes DNA which encodes manganese superoxide dismutase, thioredoxin, interleukin-12 antagonist p40(2), glutathione peroxidase, catalase, 15-lipoxygenase, interleukin-10, leptin, interleukin-4, or an antisense or ribozyme which reduces the expression of inducible nitric oxide synthase, poly-ADP-ribose polymerase, cyclooxygenase 2 or 12-lipoxygenase or any other DNA which reduces immune system-mediated cell toxicity in transduced cells. Pancreatic islet β-cells which may be protected by this method include any mammalian cell, for example, porcine, rat, murine, monkey, primate and human cells. The invention also provides adeno associated virus vectors harboring pancreatic islet β-cell cytoprotective genetic material, such as, for example, the DNA listed above.

In one embodiment, the method of protecting pancreatic islet β-cells from immune system-mediated injury involves providing pancreatic islet β-cells from, for example, a mammal such as pig, rat, mouse, monkey, primate or human, and transducing these cells with an adeno associated virus vector having inserted therein genetic material encoding a product which reduces immune system-mediated cell toxicity in the transduced cells. These transduced cells are optionally transplanted into a mammal and may be an autograft, an allograft or a xenograft. Suitable genetic material which reduces immune system-mediated cell toxicity in the transduced cells includes, without limitation, the exemplary DNA listed above.

In another embodiment, this invention provides a method of preventing rejection of transplanted pancreatic islet β-cells involving providing pancreatic islet β-cells and transducing these cells with an adeno associated virus vector having inserted therein genetic material encoding a product which reduces immune system-mediated cell toxicity in the transduced cells including, for example and without limitation, the is exemplary DNA listed above. Pancreatic islet β-cells from, for example, a mammal such as pig, rat, mouse, monkey, primate or human may be used. The transduced cells are then transplanted into a mammal as an autograft, an allograft or a xenograft.

DETAILED DESCRIPTION OF THE PREFERRED EMBODIMENTS

Applicants have developed the first method of transfecting pancreatic islet β-cells with AAV. Specifically, applicants have prepared adeno associated virus into which genes may be inserted for gene transfer into pancreatic islets. This application describes a construct useful in transfecting endogenous or exogenous pancreatic islet β-cells and in preventing graft rejection in pancreatic islet β-cell transplants. This construct consists of a cytoprotective gene, for example, manganese superoxide dismutase, thioredoxin, leptin, interleukin-12 antagonist p40(2), glutathione peroxidase, catalase, interleukin-4, interleukin-10, 15-lipoxygenase, or genetic material which eliminates or reduces the expression of inducible nitric oxide synthase, cyclooxygenase 2, poly-ADP-ribose polymerase or 12-lipoxygenase inserted into an AAV vector. The construct may be introduced into pancreatic islet β-cells prior to hetero-transplantation, or may be used to protect cells of patients removed for autotransplantation, or for primary prevention of Type 1 diabetes. It may be used for in vivo or ex vivo gene therapy of pancreatic cells.

Figure 1:
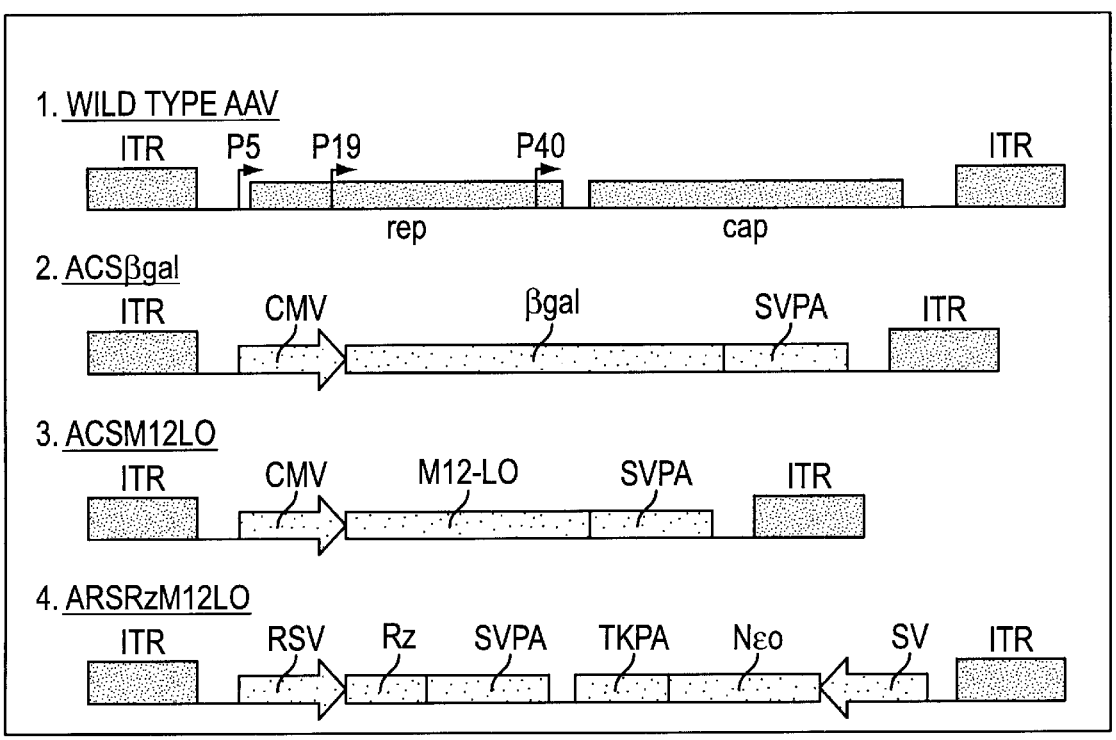
FIG. 1 shows a schematic map of exemplary AAV vectors.

FIG. 1 provides schematic diagrams of the AAV constructs used for these studies. Wild type AAV demonstrates the inverted terminal repeat sequences (ITR) at both ends flanking the rep and cap genes that encode viral elements. ACSβgal is used for demonstrating that the AAV construct can transfer the β-galactosidase gene (β-gal) to the target tissue. As shown, ACSβgal contains the AAV ITRs plus the β-gal gene linked to the SV40 poly A tail (SVPA). ACSM12-LO utilizes the standard inverted terminal repeat sequences (ITR) at both ends plus the cytomegalovirus (CMV) promoter, the mouse 12-LO DNA (M12-LO), and the SV40 poly A tail (SVPA). ARSRzM12LO is a construct for a 12-LO ribozyme which can catalytically cleave 12-LO mRNA. ARSRzM12LO contains AAV ITRs at both ends, and the respiratory syncytial virus (RSV) promoter linked to a poly A tail (SVPA). In the opposite direction, ARSRzM12-LO contains a neomycin resistance gene (Neo) linked to the herpes virus thymidine kinase poly A tail (TKPA). The Neo gene is included in order to make the AAV construct the proper size and in addition can be used to screen for neomycin resistance.

For the wild type AAV, the coding region of viral proteins (rep and cap) driven by three promoters, and inverted terminal repeats (ITR) are indicated. AAV vector ACS-βgal encodes the bacterial β-galactosidase enzyme driven by CMV promoter. ACSM12-LO encodes the mouse 12-lipoxygenase using CMV promoter. ARSRzM12LO encodes the ribozyme targeted to mouse lipoxygenase driven by RSV 3' LTR. ARSRzM12LO also encodes the neomycin resistance enzyme driven by SV40 early promoter. Polyadenylation signals, SV40 polyA (SVPA) and herpesvirus thymidine kinase polyA (TKPA) are also indicated.

Figure 2A:
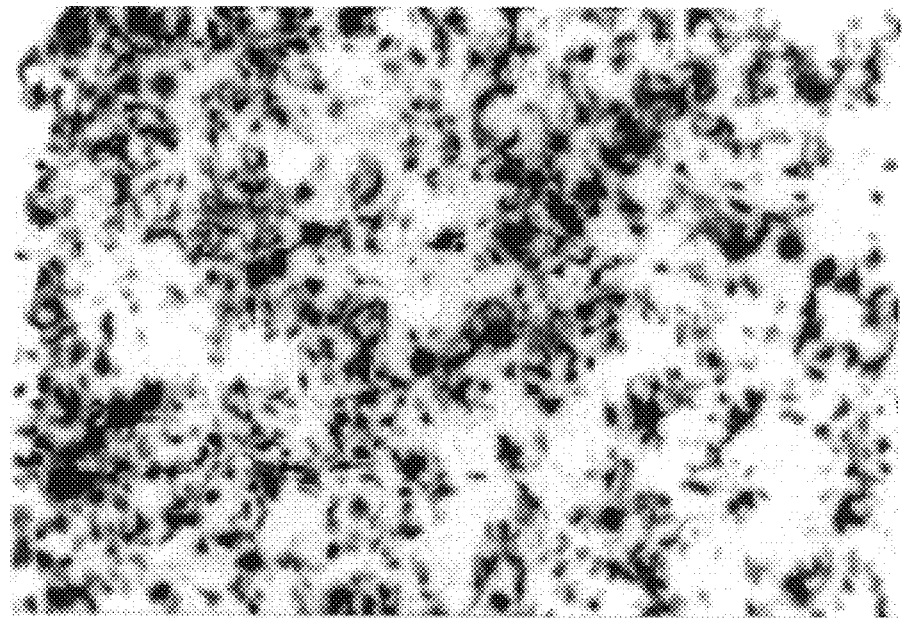
FIG. 2 shows 293 cells transduced with vAAVβgal. Panel A is a micrograph of cultured cells stained for β-gal. Panel B shows an unstained control.
Figure 2B:
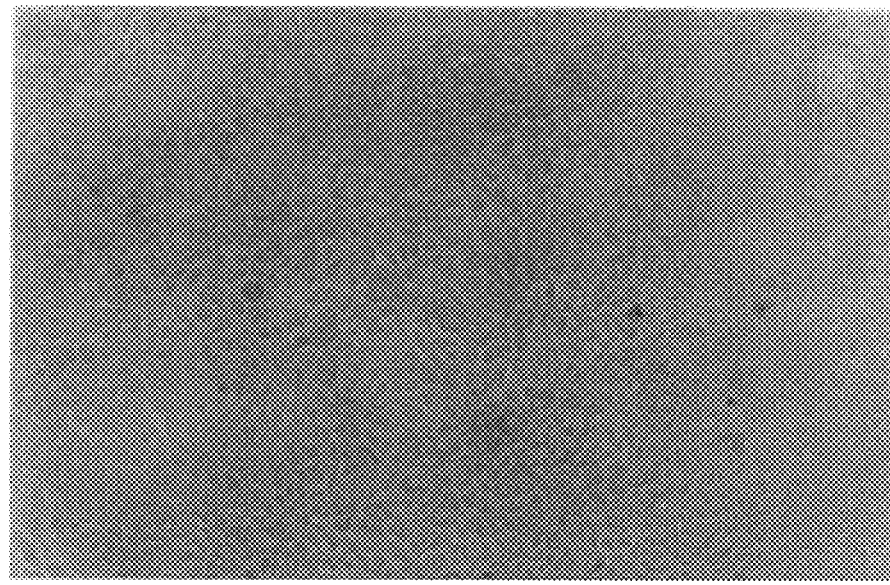
Figure 3A:
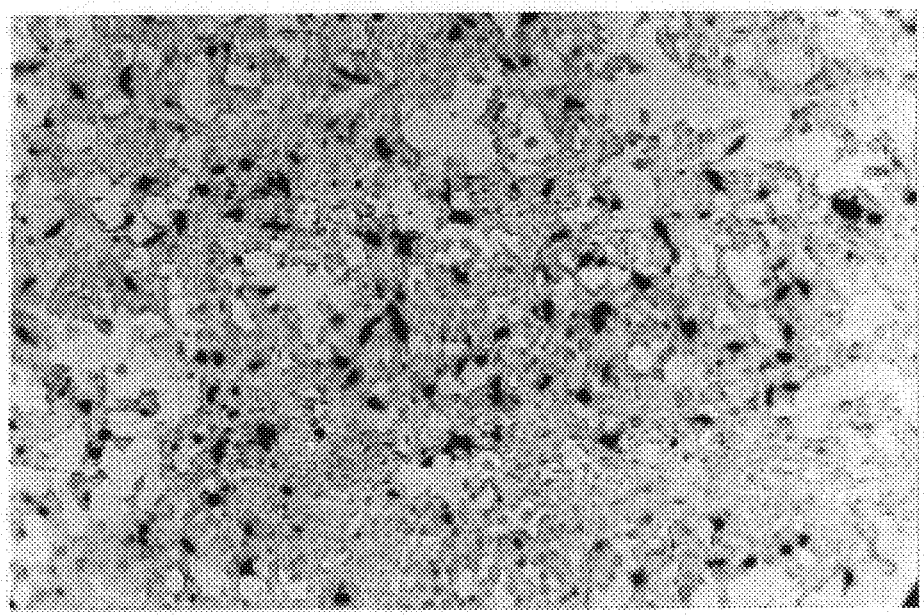
FIG. 3 shows RIN-m5F cells transduced with vAAVβgal. Panel A is a micrograph of these cells stained for β-gal. Panel B is a representative control showing unstained cells.
Figure 3B:
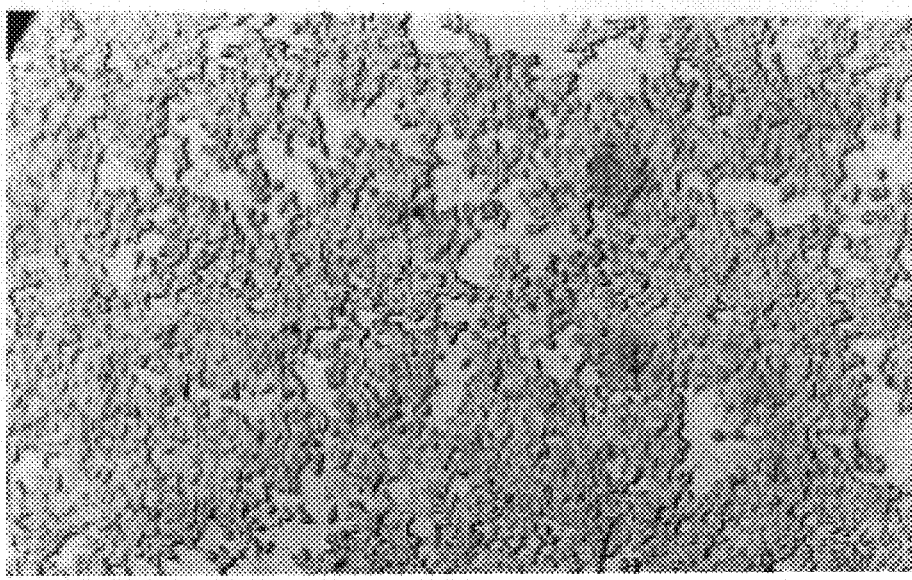
Figure 4A:
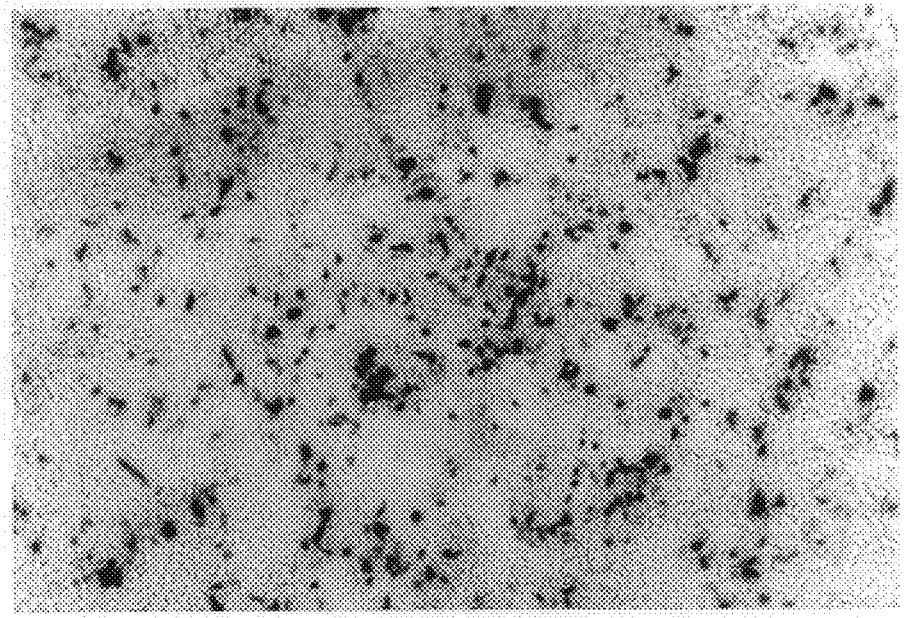
FIG. 4 shows INS-1 cells transduced with vAAVβgal. The top panel (A) shows cultured cells stained for β-gal while the bottom panel is an unstained control.
Figure 4B:
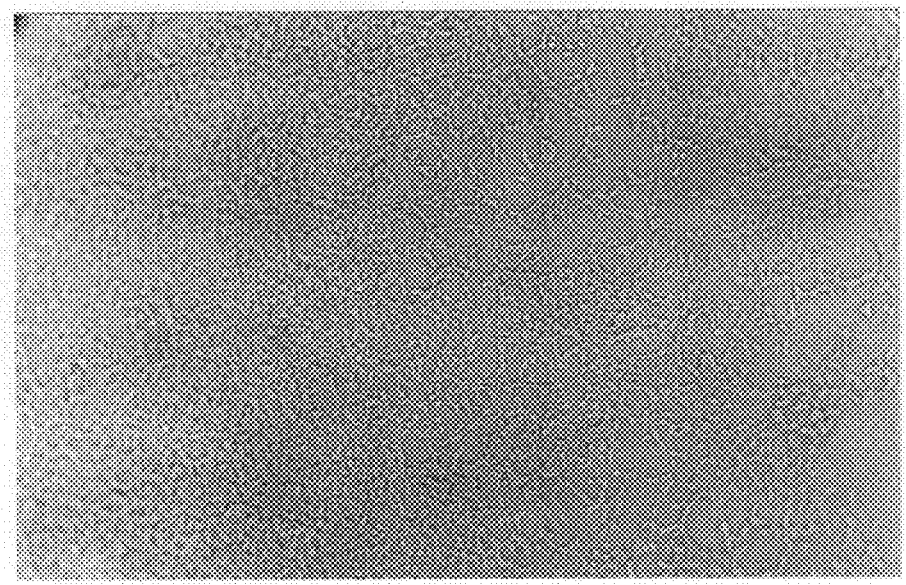

Transduction with the β-gal gene was used to test the ability of the AAV vectors to insert a gene into pancreatic β-cells. This gene is commonly used to test gene insertion and expression, and indicated the ability of AAV vectors to readily transduce pancreatic cells. The data in FIG. 2 demonstrate efficient transfer of β-gal to 293 cells using ACSβgal. The rep and cap genes which are necessary for replication and capsidation were provided in trans by the helper plasmid pAAV/Ad (Samulski, 1989). The rat insulinoma cell line RIN m5F transduced with ASLβgal with an efficiency of ~57% and the mouse insulinoma cell line INS-1 with an efficiency of ~65%. These data demonstrate the feasibility of pancreatic islet β-cell transfection with AAV vectors. See FIGS. 3 and 4.

Figure 5:
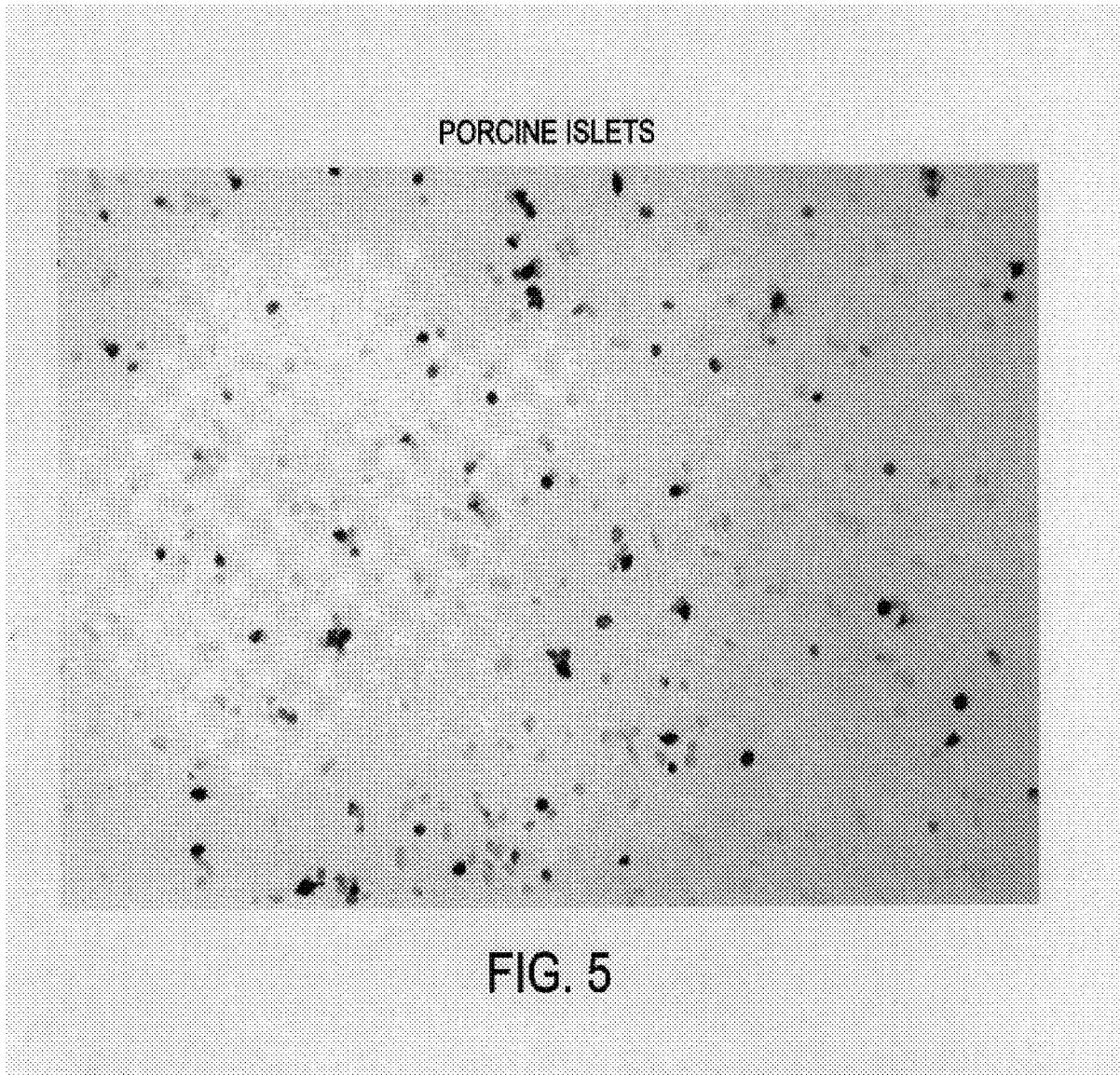
FIG. 5 is a micrograph of dispersed porcine pancreatic islets showing β-gal staining indicative of successful transfection with an AAV vector.
Figure 6A:
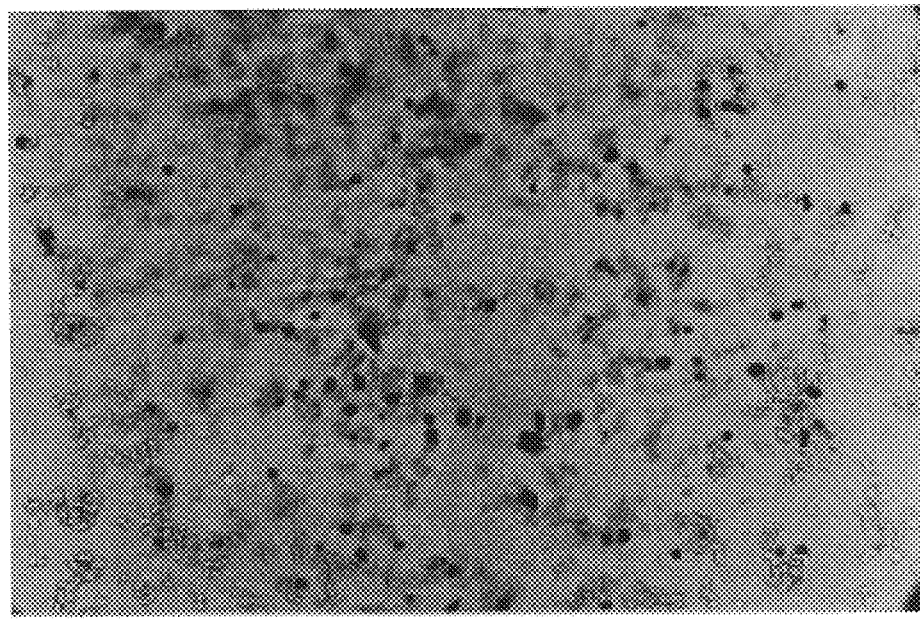
FIG. 6 depicts rat islet cells stained to show the presence of AAV transfection. Compare panel A, showing β-gal staining to the control unstained cells (panel B).
Figure 6B:
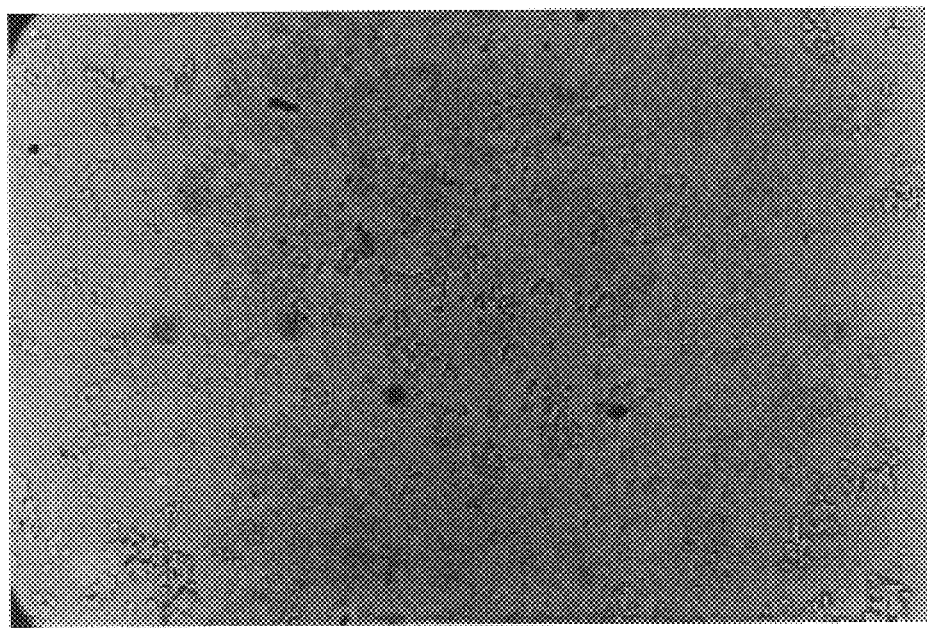

AAV constructs also efficiently transfected porcine islet cells. FIG. 5 shows dispersed porcine islets transduced with ASCβgal. The transduction efficiency is ~47%. Rat islet cells likewise were transduced using the AAV vector with high efficiency (38%). See FIG. 6.

Figure 7:
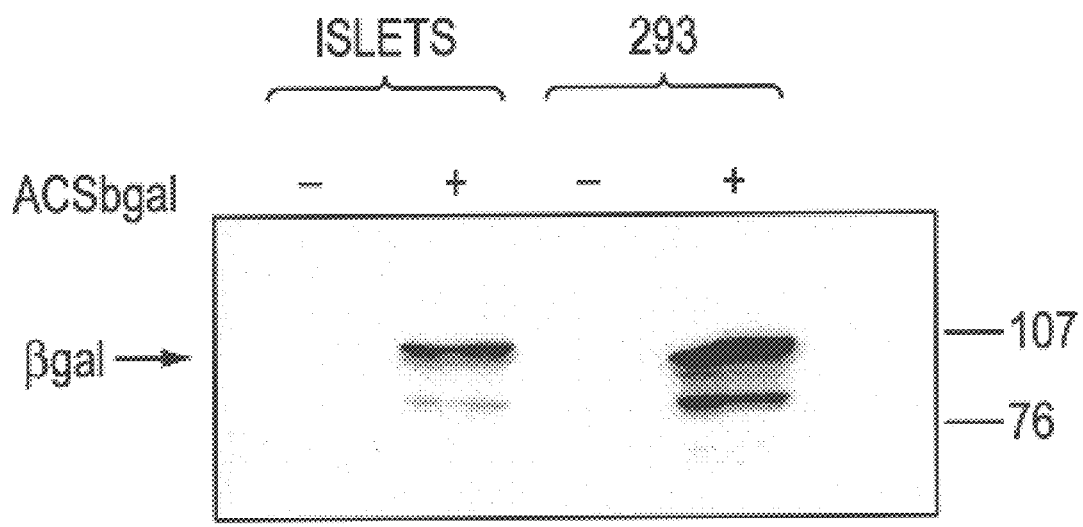
FIG. 7 is a Western blot showing AAV vector mediated β-gal expression in porcine islet cells and 293 cells. Transduced cells (+) show a band-indicative of β-gal (see arrow) while untransduced cells (−) do not.

Western blot analysis confirmed that the transfected cells expressed β-gal. See FIG. 7. Porcine islets (dispersed with collagenase and cultured overnight) or 293 cells were transduced (+) with ACSβgal at a multiplicity of infection of 10. Two days following transduction, cells were trypsinized and plated on poly-D-lysine coated chamber slides. Four days after transduction, cells were harvested. Protein extracts were analyzed by Western blot using a mouse anti-β-gal monoclonal antibody (Promega, Madison, Wis.). Untransduced cells (−) served as negative controls. Numbers on the right side of the Figure indicate molecular weight markers. Table 1 shows the transduction efficiency of various cell types transduced with AAV vectors.

TABLE 1

Transduction Efficiency of AAV Vectors

| Cells | Efficiency |
| --- | --- |
| 293 | 80% |
| RIN-m5F | 57% |
| INS-1 | 65% |
| Rat Islet cells | 38% |
| Porcine Islet cells | 47% |
| Porcine Islet β cells | 39% |

Figure 8:
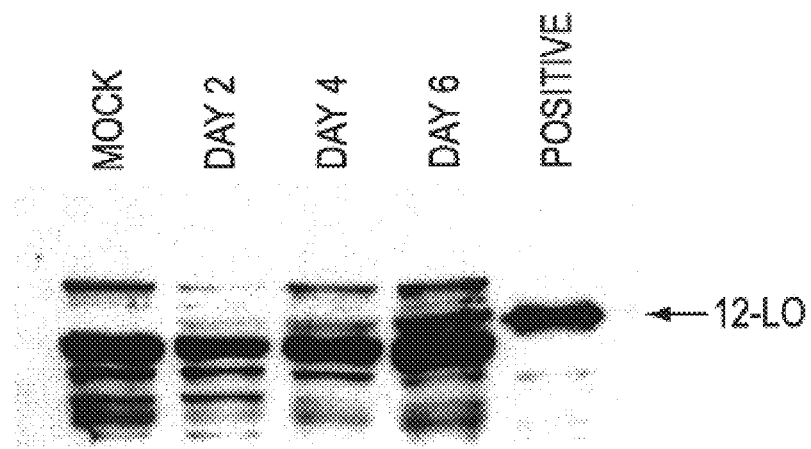
FIG. 8 is a Western blot showing the time course of AAV vector mediated 12-LO expression in porcine islet cells. The positive control shows a dark band indicative of 12-LO protein (see arrow). Mock-transfected cells served as a negative control.
Figure 9A:
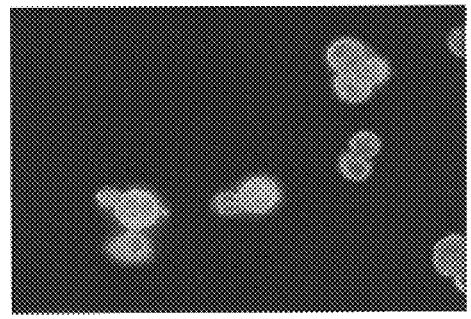
FIG. 9 shows transduced porcine islet cells stained for β-gal protein (panel A), insulin (panel B) or both (Panel C).
Figure 9B:
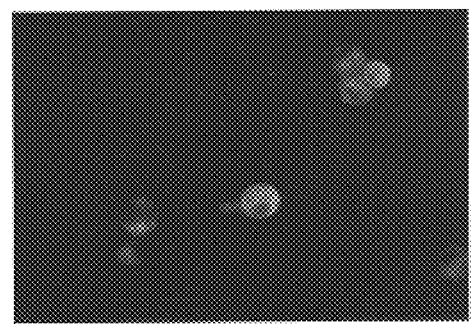
Figure 9C:
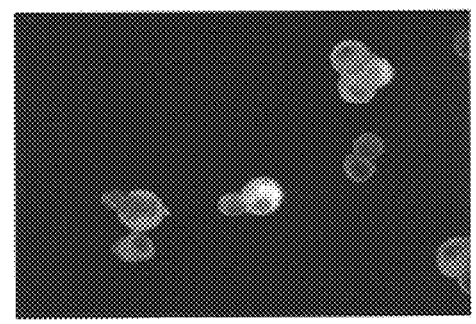

The time course of AAV vector-mediated expression of mouse 12-LO expression in porcine islet cells also was studied by Western blot. The islets were treated with ACSM 12-LO. As shown in FIG. 8, maximal expression of 12-LO protein was seen six days after viral transduction. FIG. 9 provides histocyto-chemical data showing the presence of β-gal protein in insulin producing porcine islet β-cells transduced with ACSβgal (MOI =20). Four days after transduction, the cells were fixed in preparation for double staining with mouse anti-β-gal monoclonal antibodies (Promega, Madison, Wis.) and guinea pig anti-insulin antibodies (Dako, Inc., Carpinteria, Calif.) with techniques common to the art. Secondary anti mouse IgG antibodies labeled with fluorescein and anti-guinea pig IgG antibodies labeled with rhodamine were used to visualize the cells. The cells were photographed with appropriate colored filters under a fluorescent microscope. In panel A of FIG. 9, the green color indicates the cells transduced with AAVβgal. The red-colored cells in panel B indicate insulin-positive pancreatic β-cells. Panel C was photographed with both red and green filters and shows cells which stain for both β-gal and insulin. These yellow orange cells are β-cells. Some non-i-cells also were transduced with β-gal (observe two-cells having green fluorescein fluorescence indicating β-gal, but no red rhodamine fluorescence indicating insulin. The transduction efficiency for these porcine islet β-cells was ~39%. These results indicate that AAV vectors are capable of leading to gene expression in the beta cells of the islet.

Genes which may be manipulated to protect pancreatic islet β-cells include, but are not limited to the examples contained in Table 2. These genes have been identified by the indicated references as involved in cytotoxic stress to pancreatic β-cells. Of course, any suitable gene involved in immune-induced β-cell death may be used. In Table 2, genes listed with a +indicate that overexpression of those genes is cytoprotective; genes listed with a −indicated that reduced or eliminated expression of those genes results in cytoprotection.

TABLE 2

Examples of Cytoprotective Genetic Manipulation

| Gene | Expression (+) or Reduced Expression (−) | Reference(s) |
| --- | --- | --- |
| manganese superoxide dismutase | + | Hohmeler et al., J. Clin. Invest. 101: 1811–1820 (1998) |
| thioredoxin | + | Hotta et al., J. Exp. Med. 188(8): 1445–1451 (1998) |
| interleukin-12 antagonist p40 (2) | + | Rothe et al., Diabetologia 40: 641–646 (1997); Yasuda et al., J. Clin. Invest. 102: 1807–1814 (1998) |
| glutathione peroxidase | + | Burney et al., Nitric Oxide: Biol. Chem. 1(2): 130–144 (1997); Lenzen et al., Free Radical Biol. Med. 20(3): 463:466 (1996) |
| catalase | + | Benhamou et al., Diabetologia 41: 1093–1100 (1998) |
| interleukin–4 | + | Nickerson et al., Transplant. Proc. 25(1): 984–985 (1993) |
| interleukin–10 | + | Tahara et al., Transplant. Proc. 25(6): 2975–2976 (1992) |
| leptin | + | Shimabukuro et al., J. Clin. Invest. 100(7): 1750–1754 (1997) |
| inducible nitric oxide synthase | − | Bergmann et al., FEBS Lett. 299(1): 103–106 (1992); Kolb et al., Life Sci. 49(25): 213–217 (1991); Corbet et al., Biochem. J. 299: 719–724 (1994); Delaney et al., Diabetologia 39(supp. 1): A17 (1995) |
| poly–ADP–ribose polymerase | − | Burkhart et al., Nature Med. 5(1): 314–319 (1999) |
| cyclo-oxygenase–2 | − | Nakayama et al., Proc. Natl. Acad. Sci. USA 95: 10954–10959 (1998) |

The inventors have discovered that leukocyte-type 12-LO gene expression in pancreatic β-cells is upregulated by cytotoxic cytokines (e.g., interleukin-1β). The resulting increased conversion of arachidonic acid to 12(S)-HPETE by 12-LO leads to increased lipid hydroperoxide formation when cytokines are present. In the presence of interleukin-1β, 12(S)-HPETE in particular causes increased cellular lipid peroxidation. The damage caused by peroxidation elicits the immune-mediated cytotoxic response which is partially responsible for the rejection of transplanted islet cells. The increased reduction of 12(S)-HPETE to 12(S)-HETE by glutathione peroxidase which occurs when normal intracellular stores of glutathione are depleted is related to glutamate-induced neuronal cell death. 12-LO inhibition can prevent this neuronal cell death, implicating a role for 12-LO in certain other types of mechanisms in cell death as well.

Disruption of the 12-LO pathway at a stage prior to the production of 12(S)-HPETE therefore protects islet cells from the immune-mediated cytotoxic response. According to the inventive method, AAV vectors may be used to insert a 12-LO antisense oligonucleotide or a 12-LO ribozyme which recombines with the host DNA and inhibits the 12-LO pathway. A suitable ribozyme for use with the present invention was disclosed by Gu et al., *Circulation Res.* 77(1):14–20 (1995). The destruction of 12-LO mRNA by the 12-LO ribozyme and method of the present invention achieves the purpose of effectively inhibiting conversion of arachidonic acid to 12(S)-HETE and other intermediates including 12(S)-HPETE via the 12-LO pathway. The import of reducing 12-LO gene expression in protecting against the development of Type 1 diabetes has been demonstrated. Bleich et al., *J. Clin. Invest.* 103:(in press) (1999). Like islet cells containing other protective genes, these cells can be xeno-, allo- or auto-transplanted, and will be resistant to the immune-mediated response that ultimately can cause transplant rejection.

Pancreatic cells for transplantation may be obtained from any suitable source, including for example, human, simian, murine, porcine or any other suitable species, for xenograft, allograft, or autograft. Generally, pancreas tissue is surgically removed and enzymatically digested. Islets may be picked from the pancreatic cell digest by any suitable method and cultured in various media well known in the art.

EXAMPLES

Example 1

Preparation of Pancreatic β-Cells.

For experimental purposes, mouse pancreas was surgically removed and digested with 5 ml 0.5% solution Type V collagenase (Sigma Chemical Co., St. Louis, Mo.; w/v 15 mg/30 ml) diluted in cold Hank's Balanced Saline Solution. The pancreas was minced with scissors and incubated in a shaker-type water bath at 37° C. for 8–10 minutes. The pancreatic digest then was poured into a blackbacked petri dish and islets were picked by hand.

Twenty-five mouse islets per experiment were cultured overnight in 25 mm dishes with 1.5 ml RPMI-1640 medium containing 10% FCS, 10 mM HEPES, 100 U/ml penicillin G and 100 pg/ml streptomycin. The next morning, islets were gently transferred to RPMI-1640 medium without glucose and incubated for 1 hour. At this time, the medium was sampled for insulin measurement and the medium glucose concentration was increased to 25 mM. The islets were incubated for an additional hour and the medium was sampled for later insulin measurement. Islets were cultured overnight and then treated with cytokines (IL-1β, TNF-α, and IFN-γ; R&D Systems, Minneapolis, Minn.) for 18 hours, then washed twice with RPMI-1640 medium without glucose. Glucose-stimulated insulin secretion then was assessed. Pancreas cells from any other species may be prepared in the same way, or any suitable method known to the art.

Example 2

Construction of an AAV Vector Containing a 12-LO Hammerhead Ribozyme

Plasmid pSPAAV was constructed by subcloning a full length wild type Adeno-associated virus type 2 DNA analog from pSub201 into a plasmid pSP-PL which was generated by removing a 62 base pair HindII-EcoRV fragment from pSP72 (Promega). pSPAAV was used to construct AAV vectors. A schematic map of this vector is provided in FIG. 1 (ARSRzM12LO).

The expression cassettes used in AAV vectors were generated using a vector pREP9 (Invitrogen). A 3.1 kbp SvaI-BglII fragment from pREP9 was subcloned into XbaI-BamHI site of pSP72. Into the resulting plasmid, pSTGI, a 420 bp SV40 early promoter was introduced at the upstream of the neomycin resistance gene. The resulting plasmid pSTGII contains two expression cassettes, a neomycin gene under the control of the SV40 early promoter and thymidine kinase poly A, and an empty cassette with a multiple cloning site flanked by RSV promoter and SV40 poly A. Both expression cassettes were lifted as a single unit and placed between the inverted terminal repeats (ITR) of PSPAAV in place of the rep and cap open reading frames of AAV. The resulting plasmid pSTGIII was used to construct AVRz12LO vector. A 42 base pair synthetic DNA coding for a ribozyme targeted to the nucleotide sequence of porcine 12-LO mRNA, flanked with half NheI and half XhoI sites was cloned into the NheI and XhoI site between the RSV promoter and the SV40 poly A.

Examples of vectors containing genes inserted into an AAV vector are given in FIG. 1. Those of skill in the art can readily construct such vectors with any desired gene using recombinant DNA methods, or construct suitable vectors containing any of the genes listed in Table 2 as cytoprotective. In addition, vectors containing antisense to the genes listed in Table 2 for which reduced or eliminated expression results in cytoprotection can easily be constructed in the same way by those skilled in the art of genetic manipulation. Likewise, suitable antisense oligonucleotides or ribozymes may be constructed which cleave the mRNA of these genes, resulting in reduced or eliminated expression.

Example 3

Transduction of Isolated Islet β-cells with the 12-LO Gene using an AAV Vector

Isolated porcine islets were dispersed with 0.1% collagenase and 0.05% trypsin in phosphate-buffered saline (PBS) and treated with AAV lacZ at a multiplicity of infection (MOI) of 10 for 10–14 hours. Islet cells were cultured for an additional 4 days and stained with X-gal. The percentage of cells stained blue was determined in each experiment by visual counting. The percentage of transduced islet β-cells was determined by immunohistochemical staining with both insulin specific antibodies and X-gal staining. Transduction efficiencies were 47% in dispersed porcine islet cells and 30% in intact porcine islets. Preliminary data show that 38% of the β-cells from dispersed porcine islets were transduced with AAV lacZ. In dispersed beta islet cells, 38% of cells were transduced. Beta cell lines RIN m5F and INS-1 had even higher transduction efficiencies (INS-1=65%; RIN =57%). These studies represent the first demonstration of effective transduction of an AAV vector in islets and isolated beta cells. These results suggest that use of AAV vector will provide a novel approach to gene therapy of pancreatic islets or beta cells.

Example 4

Production of Replication-Competent AAV Conveying the β-Gal Gene

To generate replication competent AAV, adenovirus type 5 infected 293 cells were cotransfected with AAV vector plasmid and helper plasmid pAAV/Ad. 293 cells were harvested 48–72 hours post-transfection and resuspended in TN buffer (10 mM Tris pH 8.0, 150 mM NaCl). The cells were lysed by freezing in an ethanol dry-ice bath and thawing. Clarified cell lysate was treated with micrococcal nuclease and subjected to cesium chloride density centrifugation (40,000 rpm for 48 hours in a SW50 rotor). The fractions containing the AAV vector (~1.38 g/cc) were collected and dialyzed against DMEM medium. Titer of the vector stock carrying the β-gal gene may be determined by infecting 293 cells with serial dilutions of vectors followed by staining with X-gal (48 hours post infection) and enumerating the β-gal positive cells.

Example 5

Transduction of Porcine Islet Cells with ACSM12-LO

Porcine islet cells (dispersed with collagenase and cultured over night) were transduced with ACSM12LO at an multiplicity of infection of 10. The following day, cells were washed once with the culture medium and split into 3 equal parts and cultured further. Cells were harvested 2, 4, or 6 days after transduction (see FIG. 8). Protein extracts were prepared from the cells and subjected to Western immunoblotting using a polyclonal antibody against porcine leukocyte 12-LO peptide with the amino acid sequence spanning 646 through 662. Mock transduced porcine islet cells transduced with ACSN and harvested 4 days after transduction served as negative control. Purified porcine 12-LO served as positive control. Location of the 12-LO is indicated on right side of FIG. 8.

What is claimed is:

1. A method for transferring genetic material to primary pancreatic islet β-cells, comprising transducing said pancreatic islet β-cells with a recombinant adeno associated virus vector wherein said pancreatic islet β-cells are transduced outside of the body.

2. A method according to claim 1, wherein said genetic material encodes a peptide sequence selected from the group consisting of manganese superoxide dismutase, thioredoxin, interleukin-12 antagonist p40(2), glutathione peroxidase, catalase, 15-lipoxygenase, interleukin-10, leptin and interleukin-4.

3. A method according to claim 1, wherein said pancreatic islet β-cell is mammalian.

4. A method according to claim 3, wherein said pancreatic islet β-cell is porcine.

5. A method according to claim 3, wherein said pancreatic islet β-cell is rat.

6. A method according to claim 3, wherein said pancreatic islet β-cell is murine.

7. A method according to claim 3, wherein said pancreatic islet β-cell is monkey.

8. A method according to claim 3, wherein said pancreatic islet β-cell is primate.

9. A method according to claim 8, wherein said pancreatic islet β-cell is human.

10. Isolated primary pancreatic islet β-cells harboring a recombinant adeno associated virus vector having inserted therein genetic material wherein said genetic material encodes a peptide sequence selected from the group consisting of manganese superoxide dismutase, thioredoxin, interleukin-12 antagonist p40(2), glutathione peroxidase, catalase, 15-lipoxygenase, interleukin-10, leptin and interleukin-4.

11. A method of transferring genetic material to primary pancreatic islet β-cells, comprising:
    (a) providing primary pancreatic islet β-cells outside of the body; and
    (b) transducing said primary pancreatic islet β-cells with a recombinant adeno associated virus vector having inserted therein genetic material wherein said genetic material encodes a peptide sequence selected from the group consisting of manganese superoxide dismutase, thioredoxin, interleukin-12 antagonist p40(2), glutathione peroxidase, catalase, 15-lipoxygenase, interleukin-10, leptin and interleukin-4.

12. A method according to claim 11, wherein said pancreatic islet β-cell is mammalian.

13. A method according to claim 12, wherein said pancreatic islet β-cell is porcine.

14. A method according to claim 12, wherein said pancreatic islet β-cell is rat.

15. A method according to claim 12, wherein said pancreatic islet β-cell is murine.

16. A method according to claim 12, wherein said pancreatic islet β-cell is monkey.

17. A method according to claim 12, wherein said pancreatic islet β-cell is primate.

18. A method according to claim 17, wherein said pancreatic islet β-cell is human.

* * * * *